(12) United States Patent
Harrell

(10) Patent No.: US 10,576,037 B2
(45) Date of Patent: Mar. 3, 2020

(54) COMPOSITIONS COMPRISING PLACENTAL COLLAGEN FOR USE IN WOUND HEALING

(71) Applicant: Carl Randall Harrell, Tarpon Springs, FL (US)

(72) Inventor: Carl Randall Harrell, Tarpon Springs, FL (US)

(73) Assignee: MAM Holdings of West Florida, L.L.C., Tarpon Springs, FL (US)

( * ) Notice: Subject to any disclaimer, the term of this patent is extended or adjusted under 35 U.S.C. 154(b) by 463 days.

(21) Appl. No.: 13/798,742

(22) Filed: Mar. 13, 2013

(65) Prior Publication Data

US 2013/0245528 A1 Sep. 19, 2013

Related U.S. Application Data

(60) Provisional application No. 61/610,570, filed on Mar. 14, 2012.

(51) Int. Cl.
| | |
|---|---|
| *A61K 9/00* | (2006.01) |
| *A61F 13/00* | (2006.01) |
| *A61L 15/32* | (2006.01) |
| *A61L 15/40* | (2006.01) |
| *A61L 27/60* | (2006.01) |
| *A61L 27/54* | (2006.01) |
| *A61L 15/44* | (2006.01) |
| *A61L 27/38* | (2006.01) |

(52) U.S. Cl.
CPC .......... *A61K 9/0014* (2013.01); *A61L 15/325* (2013.01); *A61L 15/40* (2013.01); *A61L 15/44* (2013.01); *A61L 27/3834* (2013.01); *A61L 27/54* (2013.01); *A61L 27/60* (2013.01); *A61L 2300/30* (2013.01); *A61L 2300/404* (2013.01); *A61L 2300/414* (2013.01)

(58) Field of Classification Search
CPC ....... A61K 9/0014; A61L 27/60; A61L 27/54; A61L 27/3834; A61L 15/40; A61L 15/47; A61L 15/325; A61L 2300/30; A61L 2300/414; A61L 27/24; A61L 15/32
USPC ..... 424/93.7, 17.2, 443, 448, 449, 486, 499; 602/20
See application file for complete search history.

(56) References Cited

U.S. PATENT DOCUMENTS

| | | | | |
|---|---|---|---|---|
| 5,002,071 A | * | 3/1991 | Harrell | A61K 35/50 128/897 |
| 5,219,576 A | | 6/1993 | Chu | |
| 5,436,135 A | | 7/1995 | Tayot | |
| 5,501,661 A | * | 3/1996 | Cartmell et al. | 602/58 |
| 5,698,228 A | | 12/1997 | Takai | |
| 5,800,372 A | * | 9/1998 | Bell | A61F 13/0203 128/DIG. 8 |
| 5,997,896 A | | 12/1999 | Carr, Jr. | |
| 6,710,100 B1 | * | 3/2004 | Lipman | 523/111 |
| 7,871,646 B2 | | 1/2011 | Ghinelli | |
| 7,928,280 B2 | | 4/2011 | Hariri | |
| 8,283,414 B2 | * | 10/2012 | Yu | A61K 38/10 514/17.2 |
| 8,372,439 B2 | | 2/2013 | Daniel | |
| 2004/0048796 A1 | * | 3/2004 | Hariri | A61K 35/50 424/423 |
| 2004/0057938 A1 | | 3/2004 | Ghinelli | |
| 2004/0093046 A1 | | 5/2004 | Sand | |
| 2005/0079147 A1 | | 4/2005 | Delaey | |
| 2007/0020225 A1 | * | 1/2007 | Abramson | A61K 8/981 424/78.27 |
| 2007/0021704 A1 | * | 1/2007 | Hariri | A61F 13/069 602/48 |
| 2008/0181935 A1 | * | 7/2008 | Bhatia | A61K 38/39 424/443 |
| 2008/0286378 A1 | | 11/2008 | Behrens | |
| 2009/0054350 A1 | | 2/2009 | Tayot | |
| 2009/0202616 A1 | * | 8/2009 | Chong et al. | 424/447 |
| 2010/0318048 A1 | * | 12/2010 | Hoefinghoff | A61L 15/32 604/365 |
| 2011/0130710 A1 | * | 6/2011 | Becker et al. | 604/22 |
| 2011/0218472 A1 | * | 9/2011 | Mirzadeh et al. | 602/43 |
| 2011/0257666 A1 | * | 10/2011 | Ladet et al. | 606/151 |
| 2011/0269667 A1 | * | 11/2011 | Shoseyov | A61K 45/06 514/1.8 |
| 2012/0189588 A1 | * | 7/2012 | Nahas | A61K 31/00 424/93.7 |
| 2016/0186131 A1 | * | 6/2016 | Voytik-Harbin | A61L 27/24 424/93.7 |

FOREIGN PATENT DOCUMENTS

| | | | | |
|---|---|---|---|---|
| WO | WO 9003155 A2 | * | 4/1990 | ........... A61F 13/023 |
| WO | 2004026244 | | 1/2004 | |
| WO | 2006091546 | | 8/2006 | |

OTHER PUBLICATIONS

Ji Suk Choi et al., Full Thickness Skin Wound Healing Using Human Placenta-Derived Extracelluar Matrix Containing Bioactive Molecules, Sep. 20, 2012, Tissue Engineering: Part A, vol. 19, Nos. 3 and 4, 2013, pp. 329-339.*

(Continued)

*Primary Examiner* — Kim M Lewis

(74) *Attorney, Agent, or Firm* — Pabst Patent Group LLP

(57) ABSTRACT

Provided herein is a topical wound dressing that comprises a collagen and a flexible paste. Also provided is a wound dressing with a first layer of a sterilized mixture of collagen and a second adhesive layer effective to adhere to surrounding skin and to keep the first layer in contact with the wound. In addition there is provided a wound dressing foil that comprises collagen and a plastic compound that can provide a foil shape. Furthermore, methods of dressing wounds utilizing the wound dressings and wound dressing foil are provided herein.

18 Claims, No Drawings

(56) References Cited

OTHER PUBLICATIONS

Cianfarani, et al., "Placement growth factor in diabetic wound healing altered expression and therapeutic potential", Am J Pathol., 169(4):1167-82 (2006).
Durham, et al., "Preliminary evaluation of vibriolysin, a novel proteolytic enzyme composition suitable for the debridement of burn wound eschar.", J Burn Care Rehabil., 14(5):544-51 (1993).
Kirker, et al., "Glycosaminoglycan hydrogel films as bio-interactive dressings for wound healing", Biomaterials, 23(17):3661-71 (2002).

* cited by examiner

COMPOSITIONS COMPRISING PLACENTAL COLLAGEN FOR USE IN WOUND HEALING

CROSS-REFERENCES TO RELATED APPLICATION

This non-provisional application claims benefit of priority under 35 U.S.C. § 119(e) of provisional application U.S. Ser. No. 61/610,570, filed Mar. 14, 2012, now abandoned, the entirety of which is hereby incorporated by reference.

BACKGROUND OF THE INVENTION

Field of the Invention

This invention relates to the use of collagen purified from placenta tissue in compositions designed to promote wound healing.

Description of the Related Art

There is a need for improved wound dressings. Placental collagen wound dressings have a variety of advantages, with particularly prominent advantages including promotion of blood clotting to stop bleeding, retention of moisture within the wound site, and promotion of fibroblast migration to the wound site and to accelerate the wound healing process.

An ideal wound dressing has the following characteristics: 1) preserves moisture in the wound; 2) acts as a barrier to bacteria in order to prevent secondary infections; 3) allows entry of oxygen into the wound site; 4) protects wound from toxic or particulate contaminants; 5) does not involve loss of wound tissue upon removal of dressing, such as can occur if the wound tissue migrates into the dressing and leads to an attachment between the dressing and the wound tissue; 6) good function of exudates retention; 7) non allergenic; 8) non pyrogenic; and 9) sterile.

Wound dressings comprising placental collagen exhibit these characteristics. Collagen is a major structural protein in tissues such as skin, ligaments, bones, and tendon and thus can be used to form wound dressings of myriad structural characteristics. Collagen may be crosslinked such that it forms a barrier which is impermeable to bacteria, moisture, and particulate contaminants, but allows entry of gas into the wound. Collagen does not interlock with tissue in the healing wound in such a manner that removal of the collagen dressing will lead to removal of tissue in the healing wound. Furthermore, placental collagen is particularly non-allergenic, especially in crosslinked form.

There are at least four main types of collagen, with Type I and Type III of particular relevance to the wound dressing context. Type I collagen is found in connective tissue, both hard and soft. Type III is found in wounds. According to Purna, S. K. and Babu, M. "Collagen-based dressings—a review" *Burns* (2000) 26:54-62, one of skill in the art appreciates that the use of collagens in general may promote wound healing. Collagen promotes the migration of granulocytes, macrophages, and fibroblasts such that the dermis and ultimately the epidermis can be replaced and infection minimized. Collagen further acts as a strong and durable barrier.

The prior art is deficient in wound dressings comprising placental collagen. The present invention fulfills this long-standing need and desire in the art.

SUMMARY OF THE INVENTION

The present invention relates to wound dressing comprising placental collagen. One method to prepare this collagen is described in U.S. Pat. No. 5,002,071. In one aspect, the invention provides for a topical wound dressing comprising a flexible solid paste and collagen. In another aspect, the invention provides for a wound dressing foil comprising collagen and a plastic compound effective to provide a foil shape. The collagen may be extracted by proteolytic digestion from any one or more of insoluble amnion, soluble amnion, and soluble chorion from the human placenta. The collagen may also be a commercial collagen product (e.g., ZYDERM1, ZYDERM2, or ZYPLAST from Allergan; ARTEFILL from Artes Medical; EVOLENCE from ColBar Life Science; FG-5017 from Fibrogen; and ISOLAGEN.)

In another aspect, the invention provides for a wound dressing comprising two layers. The first layer is in contact with a wound. The first layer comprises collagen. The first layer is in contact with the wound even if the entire wound is not covered by the first layer, provided that a substantial portion of the first layer is in contact with the wound. The second layer is in contact with the first layer and a portion of the skin surrounding the wound. The second layer adheres to the portion of skin surrounding the wound and is effective to maintain the first layer in contact with the wound. The second layer comprises an adhesive compound. The second layer may be in the shape of a film. The second layer may have only one side that is adhesive. The second layer may be further comprised of plastic compound.

One aspect of the invention provides for a wound dressing comprising two layers, a first and a second layer, with the first layer further comprising a hydrogel effective to retain moisture in the wound. The first layer is in contact with a wound and comprising collagen. The first layer is in contact with the wound even if the entire wound is not covered by the first layer, provided that a substantial portion of the first layer is in contact with the wound.

In yet another aspect, the invention further provides a wound dressing comprising two layers, a first layer and a second layer, wherein the first layer further comprises skin cells. The first layer is in contact with a wound and comprises collagen.

In yet another aspect, the invention further provides a wound dressing comprising two layers, a first layer and a second layer, wherein the first layer further comprises stem cells. The first layer is in contact with a wound. The first layer comprises collagen.

In yet another aspect, the invention provides for a wound dressing comprising two layers, a first layer and a second layer, wherein the first layer further comprises a blood clotting agent. The first layer is in contact with a wound. The first layer comprises collagen extracted by proteolytic digestion of one or more of the insoluble amnion, soluble amnion, and soluble chorion. Blood clotting promoting agents that may be used include fibrin, thrombin, vitamin K, and hyalurinic acid.

In yet another aspect, the invention provides a wound dressing comprising two layers. The first layer is in contact with a wound. The first layer further comprises collagen and a superabsorbent polymer.

In an alternative aspect, the invention provides a wound dressing comprising two layers, a first layer and a second layer, wherein the first layer further comprises a wound healing factor. The first layer is in contact with a wound and comprises collagen. In one aspect, the invention provides for a wound dressing comprising two layers. The first layer is in contact with a wound, comprises collagen and further comprises placental alkaline phosphatase. In yet another aspect, the invention provides for a wound dressing comprising two layers. The first layer is in contact with a wound and comprises collagen and further comprises a growth factor. In yet another aspect, the invention provides for a sponge or poultice comprising collagen that is applied to the wound. In yet another aspect, the invention provides for a wound dressing comprising collagen and growth factors.

In certain embodiments of the above aspects, the collagen is from a human source. In another embodiment the collagen is placental collagen. In yet another embodiment, the collagen is extracted from whole placenta. In yet another embodiment, the formulation is collagen in a concentration of 35 mg/mL in a saline solution that is isotonic relative to the wound tissue.

Other aspects and embodiments will be apparent to those skilled in the art form the following detailed description.

DETAILED DESCRIPTION OF THE INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. The discussion of the general methods given herein is intended for illustrative purposes only. Other alternative methods and embodiments will be apparent to those of skill in the art upon review of this disclosure.

A group of items linked with the conjunction "or" should not be read as requiring mutual exclusivity among that group, but rather should also be read as "and/or" unless expressly stated otherwise. Although items, elements, or components of the invention may be described or claimed in the singular, the plural is contemplated to be within the scope thereof unless limitation to the singular is explicitly stated.

As used herein, "a" or "an" means "at least one" or "one or more".

It is appreciated by those skilled in the art that collagen is the principal extracellular structural protein of the animal body. At least seven types of mammalian collagen have been described. Their common characteristic is a three stranded helix, consisting of 3 polypeptide chains, called alpha-chains. All chains have the same configuration, but differ in the composition and sequence of their amino acids. This leads to different types of alpha chains, but they all have glycine in every third position of the amino acid sequence. This allows the helical conformation to occur. In certain embodiments, collagen includes placental collagen, recombinant human collagen, tissue engineered human-based collagen, porcine collagen, bovine collagen, autologous collagen, collagen fibers, or human tissue collagen matrix.

In certain embodiments, "collagen layer", "collagen" or "collagenous tissue" is extracted from a human source. In certain embodiments, collagen is extracted from human placental tissue. In certain embodiments, the collagen is extracted from pooled placental tissue. In alternative embodiments, the collagen is extracted from a single placenta. This may be particularly helpful when repeated treatments of the same subject are employed. In certain embodiments, the collagen is extracted from the whole placenta. Placental tissue includes the amnion and the chorion. The collagen may be extracted according to disclosures in U.S. Pat. No. 5,002,071, which is incorporated by reference in its entirety herein. The collagen may be extracted by proteolytic extraction of any one or more of the following samples defined in U.S. Pat. No. 5,002,071: whole placenta insoluble amnion, soluble amnion, soluble chorion. Exemplary methods of preparing placental collagen for skin materials are described below as Preparations 1-5.

Compositions containing human sourced collagen are advantageous over compositions containing non-human sourced collagen, such as bovine collagen, when injected into humans. Injections of allogeneic compositions have a reduced immune response compared to injections of compositions containing material sourced from a different species than the recipient. Examples of an immune response include inflammation and release of chemicals including, histamine, bradykinin and serotonin, growth factors, cytotoxic factors, eicosanoids and cytokines. Eicosanoids include prostaglandins that produce fever and the dilation of blood vessels associated with inflammation and leukotrienes that attract certain leukocytes. Cytokines include interleukins that are responsible for communication between white blood cells; chemokines that promote chemotaxis, and interferons that have anti-viral effects, such as shutting down protein synthesis in a host cell.

It is appreciated by those of skill in the art that the collagen layer of skin comprises a mixture of Type I and Type III collagen. Type I collagen is the most abundant collagen of the human body and is the principal extracellular material present in scar tissue, tendons, skin, artery walls, the endomysium of myofibrils, fibrocartilage and the organic part of bones and teeth. Type I collagen is composed of 2 alpha1-chains and one alpha2-chains. When clinicians speak of "collagen," they are usually referring to Type 1. However, "collagen" as used herein refers to any type of collagen. For example, "collagen" may refer to only Type I, only Type III, and a mixture of Type I and Type III collagen.

Type III collagen is present in rapidly growing tissue, particularly juvenile and healing skin. This is the collagen of granulation tissue, and is produced quickly by young fibroblasts before the tougher type I collagen is synthesized.

"Placental collagen" refers to herein collagen that is purified from the placenta. Placental collagen may be purified from the insoluble amnion, the soluble amnion, or the chorion.

"Crosslinking" refers to herein the process of treating collagen to increase the level of covalent bonding among individual collagen molecules. Crosslinking may be in the form of disulfide bonds. For instance, Type III collagen has inter-chain disulfide bonds, whereas type I collagen does not. The inter-chain disulfide bonds are one type of crosslinking and can provide additional molecular stability. An increase in cross-linked type collagen may result in a longer persistence of the collagen material when used in a subject as compared to lesser or no crosslinked materials. Cross-linked collagenous tissue, in some embodiments, as compared to lesser or no cross-linked tissue may have one or more of the following characteristics: increased tensile or structural strength, increased resistance to enzymatic degradation, reduced antigenicity and reduced immunogenicity. Modes of crosslinking include exposing collagen to gamma irradiation or contacting collagen with a synthetic or natural crosslinking agent.

The terms "wound", "wound bed" or "wound area" may be used interchangeably. A wound is an area of a subject where skin normally exists but is not present. Skin is the outer covering of living tissue of an animal. In some embodiments, the subject has a wound area caused by an event or condition that results in loss of skin and exposure of flesh or tissue not normally exposed. Non-limiting examples include trauma, injury, infection, disease, surgery or burn. In certain instances, the wound is any portion of the body that would benefit from the application of the skin material composition or methods of grafting skin as presented herein. Benefits include protecting the subject against pathogens, insulation, temperature regulation, synthesis of vitamin D, water resistance, protection and correction of an otherwise disfiguring or aesthetically undesirable appearance.

"Terminal sterilization", as used herein, is described in U.S. patent application Ser. No. 11/383,845, published on Dec. 14, 2006 as U.S. Patent Application 2006/0280769, which is incorporated herein by reference. In particular embodiments, the collagen in the skin material compositions may be treated by terminal sterilization. In specific embodiments, this method further comprises freezing the collagen material and irradiating the collagen material with an effective amount of gamma or electron beam radiation to sterilize the collagen material without causing significant deterioration of the collagen material. Gamma ray or e-beam radiation is at least 5 kGy, or between 6 kGy and 8 kGy. In some embodiments, the collagen of the skin material for grafting is sterilized prior to contact with the skin material. In some embodiments, the collagen is sterilized immediately prior to contact with the wound or harvested skin. In other embodiments, the collagen after sterilization is stored and handled under sterile conditions prior to contact with the wound.

General Embodiments

Subjects that will respond favorably to the methods disclosed herein include medical and veterinary subjects generally, including mammals and specifically human patients. Subjects include dogs, cats, horses, sheep, cows, pigs, rabbits, rodents, mice, and rats. In general, any subject who would benefit from the composition and methods of the invention relating to skin grafts are appropriate for administration of the invention method.

In certain embodiments of the various wound dressings described herein, the collagen is substantially free of noncollagenous proteins. When using collagen as a biomaterial, it is important to use it in its purest and crystalline form to eliminate the noncollagenous proteins that are far more potent antigens. Once the inflammatory cycle is stimulated, the resorption of collagen occurs by the infiltrating inflammatory cells, principally macrophages and, to a lesser extent, granulocytes. These cells contain collagenase which acts to digest collagen. Skin collagen is chemotactic itself and becomes even more active by digestion with tissue collagenase into smaller peptide fragments. Chemotropism is the attraction of living protoplasm to chemical stimuli whereby the cells are attracted (positive hemotaxis) or repelled (negative chemotaxis) by acids, alkalis or other bodies exhibiting chemical properties. Various types of collagens, their alpha-chains, as well as small peptides formed by collagenase digestion have been shown to be chemotactic to dermal fibroblasts. Chemotactic migration of fibroblasts into the site of tissue injury or theoretically injected collagen can be regulated by the solubilized collagen or its degradation products. Thus, a collagen implant would not remain dormant in the tissue but a complex series of events may occur. First, the collagen implant could be invaded by inflammatory cells and fibroblasts and, while being continuously resorbed, it could promote an inflammatory reaction by chemotactic properties of its degradation products. Thus, the area of collagen metabolism is not only important for collagen and other soft tissue injectable materials, but also to both normal and abnormal wound healing (i.e. hypertrophic scarring and keloids).

Placental Collagen Topical Wound Dressing with Flexible Solid Paste

In one aspect, the invention provides for a topical wound dressing comprising collagen extracted by proteolytic digestion from at least one or more of the amnion, soluble amnion, soluble chorion from human placenta. The topical wound dressing is also comprised of a flexible solid paste. In some embodiments the flexible solid paste may be zinc oxide. In some embodiments, the flexible solid paste may be thickened honey or sugar paste. In some embodiments, the thickened honey or sugar paste further comprises adhesive polymers such that the thickened paste has suitable viscoelastic properties to prevent hypergranulation and scarring. In some embodiments, the flexible solid paste comprises one or more of the following: starch, mannitol, cellulose, magnesium stearate, magnesium carbonate, hydrocolloids, hydrogels, foams, and silver.

The topical wound dressing may be applied to a wound and covered with a barrier layer, such as gauze or a plastic film.

Type I and Type III Collagen

In some embodiments the topical wound dressing comprises a mixture of Type I and Type III collagen. The ratio of Type III to Type I collagen is equal to or greater than 30:70, 40:60, 45:55, 50:50, 55:45, 60:40, 65:35, 70:30, 75:25, 80:20, 85:15, 90:10, or 95:5.

Type III collagen is found in several types of connective tissue throughout the human body, with its proportion high in young tissue, such as tissue formed during the early phases of wound healing. Wound dressings with a high ratio of type III collagen to type I collagen may thus be particularly useful as they more closely mimic endogenous tissue. Wound dressings containing type III collagen may be useful in reducing the formation of excess scar tissue in wound healing by signaling to endogenous skin cells that there is sufficient scar tissue or young tissue already formed. Increasing the ratio of type I to type III collagen may be useful to enhance the durability and strength of the wound dressing.

In certain embodiments, skin materials with collagen layers having a high ratio of type III collagen to type I collagen may thus be particularly useful as they more closely mimic endogenous tissue. In certain embodiments, skin materials containing type III collagen may be useful in reducing the formation of excess scar tissue in wound healing by signaling to endogenous skin cells that there is sufficient scar tissue or young tissue already formed. Increasing the ratio of type I to type III collagen may be useful to enhance the durability and strength of the skin material.

In certain embodiments, Type III collagen is at least 30%, 40%, 50%, 60%, 70%, 80%, 90% or 95% of the weight or volume of the collagen component.

In one embodiment, Type I and Type III collagen are present in a 50%:50% ratio. In some embodiments, the Type I and Type III collagen are present in a 50%:50% ratio, with a total collagen concentration of 35 mg/mL in saline solution that is isotonic relative to the wound tissue.

Crosslinking

In some embodiments, either one or both of Type I or Type III collagen may be crosslinked. In some embodiments, Type I collagen is crosslinked and Type III collagen is crosslinked. In some embodiments, Type I is non-crosslinked and Type III collagen is noncrosslinked. In some embodiments, Type I collagen is crosslinked and Type III collagen is noncrosslinked. In some embodiments, Type I collagen is non-crosslinked and Type III collagen is crosslinked.

In some embodiments, the collagen is cross-linked by gamma irradiation. In some embodiments, the collagen is exposed to gamma irradiation of at least 0.20 M rads. In some embodiments, the gamma irradiation is in the range of 0.25 M rads to 2.0 M rads. In some embodiments, the gamma irradiation is in the range of 6 kGy and 8 kGy.

Terminal Sterilization

In some embodiments, the topical wound dressing is further treated by terminal sterilization according to disclosures in U.S. patent application Ser. No. 11/383,845, which is incorporated herein by reference. Terminal sterilization is effective to reduce the level of active biological contaminants without adversely affecting the collagen material. According to the methods described herein, the collagen paste, gel, solution or suspension will keep the same fluidity before and after its terminal sterilization.

The dermal fillers and injectable collagen material may be decontaminated or sterilized without significantly affecting the physiological properties of the collagen using gamma or electron-beam radiation. The mixture is irradiated under conditions that inactivate any pathogenic microorganisms, viruses, and polynucleotide fragments thereof, DNA or RNA, whether single or double stranded present within the mixture.

Gamma ray or electron beam radiation differs depending upon the density of the collagen wound dressing, but is preferably at least 5 kGy. Irradiation of more that 12 kGy is not preferred because the collagen wound dressing may be damaged. The most preferred exposure is between about 6 kGy and 8 kGy.

The collagen wound dressing that is sensitive to radiation is treated to protect it from the radiation, then irradiated for a time and at a rate effective to sterilize the filler or injectable material. In the preferred embodiment, the collagen wound dressing that is sensitive to radiation is first frozen at a temperature below its freezing temperature, which is generally below 0° C., and irradiated with a suitable radiation at an effective rate for a time effective to sterilize the collagen wound dressing. In an alternative embodiment, cryoprotectants and/or stabilizers like mannitol, mannose, ascorbic acid, hyaluronic acid, or other saccharides or polysaccharides are added to the initial collagen material before its freezing. These protecting agents are neither sufficient in the absence of freezing, nor necessary to get significant protection from irradiation, but may be advantageous.

The irradiated collagen wound dressing can be analyzed by SDS polyacrylamide gel electrophoresis and/or differential scanning calorimetry to select the optimal irradiation conditions and demonstrate the preserved quality of the collagen molecules. As used herein, without significant damage means that less than 25%, more preferably 15% or less, of the collagen wound dressing is deteriorated or degraded.

The collagen wound dressing, once sterilized, is maintained in a sterile surrounding until used by a caregiver. Illustrative containers include vials, plates, pouches, jars, syringes, etc. Preferably, the container is transparent to both gamma-rays and electron-beams.

Additives to the Topical Wound Dressing

In some embodiments, the topical wound dressing is further comprised of one or more of the following in addition to the collagen compounds and a flexible solid paste: an antibacterial compound, an antifungal compound, a macromolecule that promotes tissue regeneration, a growth factor, and an anti-inflammatory.

In some embodiments, the topical wound dressing further comprises an antibacterial agent. Exemplary antibacterial agents include, but are not limited to, iodine, penicillin, silver compounds, and erythromycin. One of skill in the art would appreciate that the antibacterial compound may be any compound effective to inhibit bacterial growth in a wound.

In some embodiments, the topical wound dressing further comprises a macromolecule that promotes tissue regeneration in the wound. Preferably such a macromolecule is effective to inhibit scar tissue formation. Exemplary macromolecules include, but are not limited to, any one or more of the following: hyaluronic acid, fibronectin, laminin, and protoglycans.

In some embodiments, the two-layer wound dressing further comprises a growth factor. The growth factor is exemplified by any one or more of the following: PDGF, EGF, TGF-alpha, TGF-beta, IGF-1, and insulin; others may also be used as is understood in the art.

In some embodiments, the two-layer wound dressing further comprises an anti-inflammatory compound. One exemplary anti-inflammatory compound is a steroid. An exemplary anti-inflammatory compound is hydrocortisone. Other anti-inflammatory compounds may also be used as is understood in the art.

Wound Dressing Foil

In another aspect, the invention provides for a wound dressing foil comprising collagen and a plastic compound effective to provide a foil shape. In certain embodiments, the collagen may be extracted by proteolytic digestion from any one or more of insoluble amnion, soluble amnion, and soluble chorion from the human placenta.

Various plastic compounds may be used to create the foil such that it can adhere to the wound and has a flat thin surface. The wound dressing foil may be particularly useful for the treatment of severe burn wounds. The plastic wound dressing foil may use a plastic that serves to allow sufficient oxygen to reach the wound site. The wound dressing foil may use a plastic that is known in the art that is permeable to oxygen and other gases but is impermeable to water such that water is retained water in the wound so as to minimize dehydration of the wound.

The collagen in the wound dressing foil may be extracted by proteolytic digestion of one or more of the following: insoluble amnion from human placenta, soluble amnion from human placenta, and soluble chorion from human placenta. In some embodiments, the collagen of the wound dressing foil is a mixture of Type I and Type III collagen. The ratio of Type III to Type I collagen is equal to or greater than 30:70, 40:60, 45:55, 50:50, 55:45, 60:40, 65:35, 70:30, 75:25, 80:20, 85:15, 90:10, or 95:5.

In some embodiments of the foil wound dressing, either one or both of Type I or Type III collagen may be cross-linked. In some embodiments, Type I collagen is crosslinked and Type III collagen is crosslinked. In some embodiments, Type I is non-crosslinked and Type III collagen is non-crosslinked. In some embodiments, Type I collagen is crosslinked and Type III collagen is non-crosslinked. In some embodiments, Type I collagen is non-crosslinked and Type III collagen is crosslinked. In some embodiments, the collagen is cross-linked by gamma irradiation. In some embodiments, the collagen is exposed to gamma irradiation of at least 0.20 M rads. In some embodiments, the gamma irradiation is in the range of 0.25 M rads to 2.0 M rads. In some embodiments, the gamma irradiation is in the range of 6 kGy and 8 kGy. In some embodiments of the foil wound dressing, the collagen is terminally sterilized.

Two-Layer Wound Dressing

In another aspect, the invention provides for a wound dressing comprising two layers. The first layer is in contact with a wound and comprises collagen. In certain embodiments, the collagen is extracted by proteolytic digestion of one or more of insoluble amnion, soluble amnion, and soluble chorion. The second layer is in contact with the first layer and a portion of the skin surrounding the wound. The second layer adheres to the portion of skin surrounding the wound and is effective to maintain the first layer in contact with the wound. The second layer may be in the shape of a film. The second layer may have only one side that is adhesive. The second layer may be further comprised of plastic compound. The first layer is in contact with the wound even if the entire wound is not covered by the first layer, provided that a substantial portion of the first layer is in contact with the wound.

In some embodiments of the wound dressing, the collagen is extracted by proteolytic digestion of one or more of the following: insoluble amnion from human placenta, soluble amnion from human placenta, and soluble chorion from human placenta. In some embodiments, the collagen of the wound dressings is a mixture of Type I and Type III collagen. The ratio of Type III to Type I collagen is equal to or greater than 30:70, 40:60, 45:55, 50:50, 55:45, 60:40, 65:35, 70:30, 75:25, 80:20, 85:15, 90:10, or 95:5.

In some embodiments of the wound dressing, either one or both of Type I or Type III collagen may be crosslinked. In some embodiments, Type I collagen is crosslinked and Type III collagen is crosslinked. In some embodiments, Type I is non-crosslinked and Type III collagen is non-crosslinked. In some embodiments, Type I collagen is crosslinked and Type III collagen is non-crosslinked. In some embodiments, Type I collagen is non-crosslinked and Type III collagen is crosslinked. In some embodiments, the collagen is cross-linked by gamma irradiation. In some embodiments, the collagen is exposed to gamma irradiation of at least 0.20 M rads. In some embodiments, the gamma irradiation is in the range of 0.25 M rads to 2.0 M rads. In some embodiments, the gamma irradiation is in the range of 6 kGy and 8 kGy.

In some embodiments, the first layer in the two-layer wound dressing is comprised of one or more of the following in addition to the collagen compounds: an excipient, an antibacterial compound, an antifungal compound, a macromolecule that promotes tissue regeneration, a growth factor, and an anti-inflammatory.

In some embodiments of the wound dressing, the first layer of the wound dressing further comprises an excipient. Exemplary excipients include, but are not limited to zinc oxide, starch, mannitol, cellulose, magnesium stearate, and magnesium carbonate.

In some embodiments, the first layer of the wound dressing further comprises zinc oxide.

In some embodiments, the first layer of the wound dressing further comprises an antibacterial agent. Exemplary antibacterial agents include, but are not limited to, iodine, penicillin, silver compounds, and erythromycin. One of skill in the art would appreciate that the antibacterial compound may be any compound effective to inhibit bacterial growth in a wound.

In some embodiments, the two-layer wound dressing further comprises a macromolecule that promotes tissue regeneration in the wound. Preferably such a macromolecule is effective to inhibit scar tissue formation. Exemplary macromolecules include, but are not limited to, any one or more of the following: hyaluronic acid, fibronectin, laminin, and proteoglycans.

In some embodiments, the two-layer wound dressing further comprises a growth factor. The growth factor is exemplified by any one or more of the following: PDGF, EGF, TGF-alpha, IGF-1, and insulin; others may also be used as is understood in the art.

In some embodiments, the two-layer wound dressing further comprises an anti-inflammatory compound. One exemplary anti-inflammatory compound is a steroid. An exemplary anti-inflammatory compound is hydrocortisone. Other anti-inflammatory compounds may also be used as is understood in the art.

Two-Layer Wound Dressing with Hydrogel Compound and Plastic Compound

Another aspect of the invention provides for a wound dressing comprising two layers, a first and a second layer, with the first layer further comprises a hydrogel effective to retain moisture in the wound. The first layer is in contact with a wound and comprises collagen. In certain embodiments, the collagen is extracted by proteolytic digestion of one or more of the insoluble amnion, soluble amnion, and soluble chorion. The first layer is in contact with the wound even if the entire wound is not covered by the first layer, provided that a substantial portion of the first layer is in contact with the wound.

The second layer is in contact with the first layer and a portion of the skin surrounding the wound. The second layer adheres to the portion of skin surrounding the wound and is effective to maintain the first layer in contact with the wound. The second layer further comprises a plastic compound that is effective to reduce the rate of water evaporation from the wound dressing.

Hydrogels absorb water and may serve to reduce the rate of dehydration from a wound. One of skill in the art may combine a hydrogel with collagen such that the collagen retains its stability and the hydrogel is effective to absorb and retain moisture close to the healing wound. The hydrogel chosen may be effectively sterilized by the terminal sterilization procedure that may be used to treat collagen immediately before application to the wound.

The plastic chosen in the second layer is also effectively sterilized by the terminal sterilization that may be used to treat collagen immediately before application to the wound. The plastic layer need not be fully impermeable to water or water vapor, but only sufficiently impermeable so as to significantly reduce the rate of evaporation.

Two Layer Dressing with Skin Cells

In yet another aspect, the invention provides a wound dressing comprising two layers, a first layer and a second layer, wherein the first layer further comprises skin cells. The first layer is in contact with a wound and comprises collagen. In certain embodiments, the collagen is extracted by proteolytic digestion of one or more of the insoluble amnion, soluble amnion, and soluble chorion.

The second layer is in contact with the first layer and a portion of the skin surrounding the wound. The second layer adheres to the portion of skin surrounding the wound and is effective to maintain the first layer in contact with the wound.

In some embodiments, either one or both of Type I or Type III collagen may be crosslinked. In some embodiments, Type I collagen is crosslinked and Type III collagen is crosslinked. In some embodiments, Type I is non-crosslinked and Type III collagen is noncrosslinked. In some embodiments, Type I collagen is crosslinked and Type III collagen is noncrosslinked. In some embodiments, Type I collagen is non-crosslinked and Type III collagen is crosslinked. In some embodiments, the collagen is cross-linked by gamma irradiation. In some embodiments, the collagen is exposed to gamma irradiation of at least 0.20 M rads. In some embodiments, the gamma irradiation is in the range of 0.25 M rads to 2.0 M rads. In some embodiments, the gamma irradiation is in the range of 6 kGy and 8 kGy.

In some embodiments, the topical wound dressing is further treated by terminal sterilization as described above.

The wound dressing with skin cells provides for alternative embodiments involving different types of skin cells. The skin cells may be living cells or nonliving cells. The skin cells may be from the epidermis or the dermal layer. Additionally, the skin cells may be stem cells. Such stem cells may be epidermal stem cells or dermal stem cells. The stem cells may be hair follicle bulge stem cells, which are particularly effective in promoting wound healing. The above types of skin cells may be effective to promote epithelialization of the healing wound.

In any of the following embodiments, the skin cells may be effective to promote epithelialization of the healing wound. In some embodiments, the skin cells may be stem cells. In some embodiments, the skin cells may be epidermal stem cells. In some embodiments, the skin cells may be dermal stem cells. In some embodiments, the stem cells may be hair follicle bulge stem cells.

A healing wound involves migration of two cell types, the dermal and epidermal cells. Without wishing to be bound by theory, dermal cells migrate from mesenchymal tissue beneath the healing wound to form dermal tissue while epidermal cells migrate laterally from the epidermis next to the wound. Formulation of granulation tissue allows speedier migration of epidermal cells into the wound. However, any of the other aspects of the invention directed to placental collagen wound dressings may further include live epidermal cells that can be used to form the epidermis more quickly by minimizing the need for extensive lateral migration of epidermal tissue from outside the wound. A desired effect of this aspect of the invention is the minimization of scar tissue formation.

Two Layer Dressing with Stem Cells

In yet another aspect, the invention provides a wound dressing comprising two layers, a first layer and a second layer, wherein the first layer further comprises stem cells. The first layer is in contact with a wound and comprises collagen. In certain embodiments, the collagen is extracted by proteolytic digestion of one or more of the insoluble amnion, soluble amnion, and soluble chorion.

The stem cells may be living cells or nonliving cells. Exemplary stem cells that may be used in some embodiments include, but are not limited to, dermal stem cells, hair follicle bulge stem cells, placenta stem cells, and cord blood stem cells. The above types of skin cells may be effective to promote epithelialization of the healing wound.

The second layer is in contact with the first layer and a portion of the skin surrounding the wound. The second layer adheres to the portion of skin surrounding the wound and is effective to maintain the first layer in contact with the wound.

In some embodiments of the two-layer wound dressing with stem cells, either one or both of Type I or Type III collagen may be crosslinked. In some embodiments, Type I collagen is crosslinked and Type III collagen is crosslinked. In some embodiments, Type I is noncrosslinked and Type III collagen is non-crosslinked. In some embodiments, Type I collagen is crosslinked and Type III collagen is non-crosslinked. In some embodiments, Type I collagen is non-crosslinked and Type III collagen is crosslinked. In some embodiments, the collagen is cross-linked by gamma irradiation. In some embodiments, the collagen is exposed to gamma irradiation of at least 0.20 M rads. In some embodiments, the gamma irradiation is in the range of 0.25 M rads to 2.0 M rads. In some embodiments, the gamma irradiation is in the range of 6 kGy and 8 kGy.

In some embodiments, the wound dressing is further treated by terminal sterilization as described above.

In some embodiments, the wound dressing first layer further comprises hair follicle stem cells. The hair follicle bulge serves as a source of stem cells for a variety of skin types. A wound dressing may be prepared with placental collagen upon which hair follicle stem cells are added. The hair follicle stem cells can then give rise to various cell types that may be deficieint in the healing wound in order to promote wound healing.

Stem cells promote healing of a wound and may allow for propagation of epithelial and dermal cells that form skin that has the appearance of normal skin rather than scar tissue. Thus, any of the above embodiments may exhibit reduced scar tissue formation as compared to collagen wound dressings without stem cells.

Two Layer Dressing with Blood Clotting Agent

In yet another aspect, the invention provides for a wound dressing comprising two layers, a first layer and a second layer, wherein the first layer further comprises a blood clotting agent. The first layer is in contact with a wound and comprises collagen. In certain embodiments, the collagen is extracted by proteolytic digestion of one or more of the insolubleamnion, soluble amnion, and soluble chorion. Blood clotting promoting agents that may be usedinclude fibrin, thrombin, vitamin K, and hyalurinic acid.

The second layer is in contact with the first layer and a portion of the skin surrounding the wound. The second layer adheres to the portion of skin surrounding the wound and is effective to maintain the first layer in contact with the wound.

The wound dressing of this aspect may be effective for stopping blood loss in a wound. The wound dressing may be used on wounds with an acute high rate of blood loss or on wounds with chronic low rate of blood loss. The blood clotting agents are effective to promote blood clotting at the site of the wound, without risking formation of blood clots in other areas of the body.

Two Layer Dressing with Blood Absorption Polymer

In yet another aspect, the invention provides a wound dressing comprising two layers. The first layer is in contact with a wound. The first layer further comprises collagen and a superabsorbent polymer. In certain embodiments, the collagen is extracted by proteolytic digestion of one or more of the insoluble amnion, soluble amnion, and soluble chorion. The second layer is in contact with the first layer and a portion of the skin surrounding the wound. The second layer adheres to the portion of skin surrounding the wound and is effective to maintain the first layer in contact with the wound.

The wound dressing of this aspect may be effective for absorbing blood in a bleeding wound. This wound dressing may result in less frequent changing of the wound dressing, since there is less accumulated blood which would interfere with the ability of the wound dressing to adhere to the wound.

In some embodiments, the superabsorbent polymer is any one or more of crosslinked polyacrylic acid, crosslinked polyacrylamide, crosslinked polyvinyl alcohol, crosslinked polyvinyl pyrrolidone, guar gum, and crosslinked polyethylene oxide.

Two Layer Dressing with Wound Healing Factors

In an alternative aspect, the invention provides a wound dressing comprising two layers, a first layer and a second layer, wherein the first layer further comprises a wound healing factor. The first layer is in contact with a wound and comprises collagen. In certain embodiments, the collagen is extracted by proteolytic digestion of one or more of the insoluble amnion, soluble amnion, and soluble chorion.

The second layer is in contact with the first layer and a portion of the skin surrounding the wound. The second layer adheres to the portion of skin surrounding the wound and is effective to maintain the first layer in contact with the wound. In some embodiments, the wound healing factor is one or more of hyaluronic acid, fibronectin, laminin, proteoglycans. In some embodiments, a mixture of wound healing factors may be used.

Two Layer Dressing with Placental Alkaline Phosphatase

In one aspect, the invention provides for a wound dressing comprising two layers. The first layer is in contact with a wound and further comprises placental alkaline phosphatase. The first layer comprises collagen. In certain embodiments, the collagen is extracted by proteolytic digestion of one or more of the insoluble amnion, soluble amnion, and soluble chorion. The second layer is in contact with the first layer and a portion of the skin surrounding the wound. The second layer adheres to the portion of skin surrounding the wound and is effective to maintain the first layer in contact with the wound.

Alkaline phosphatases are highly expressed in healing wounds. Additional placental alkaline phosphatase in the wound dressing may stimulate wound healing.

Two Layer Dressing with Growth Factors

In yet another aspect, the invention provides for a wound dressing comprising two layers. The first layer is in contact with a wound and further comprises a growth factor. The first layer comprises collagen. In certain embodiments, the collagen is extracted by proteolytic digestion of one or more of the insoluble amnion, soluble amnion, and soluble chorion.

Growth factors that may be used with the invention include PDGF, EGF, TGF-alpha, TGF-beta, IGF-I, and insulin. One or more growth factors can be used in this aspect of the invention.

The second layer is in contact with the first layer and a portion of the skin surrounding the wound. The second layer adheres to the portion of skin surrounding the wound and is effective to maintain the first layer in contact with the wound.

The use of a growth factor may stimulate wound healing. The use of a growth factor may also reduce the formation of scar tissue in the healing wound.

Sponge or Poultice

In yet another aspect, the invention provides for a sponge or poultice comprising placental collagen that is applied to the wound. A sponge is particularly advantageous for draining and bleeding wounds, since the sponge will remove the excess drainage and reduce the risk of infection. A poultice is particularly advantageous for large wounds where the risk of water loss through the wound is high due to lack of skin. A poultice may maintain moisture at the healing wound in order to reduce water loss and to promote healing.

Combine Collagen with Growth Factors

In yet another aspect, the invention provides for a wound dressing comprising placental collagen and growth factors. While one of skill in the art would appreciate that collagen can promote migration of certain cell types, such as fibroblasts, there is an additional need for growth factors to promote differentiation.

In some embodiments of this aspect, the growth factor is epidermal growth factor. The epidermal growth factor may be particularly advantageous in wounds with a large surface area, since epithelialization of the wound is a slow process that may not be accelerated by the presence of collagen alone.

In some embodiments, the growth factor includes PDGF, EGF, TGF-alpha, TGFbeta, IGF-I, insulin, and any combination of these growth factors. In some embodiments, the growth factor is covalently conjugated to the placental collagen. Chemical crosslinking may be used to conjugate the growth factor to the placental collagen.

Antibacterial Agents

In some embodiments, any of the above-described two-layer wound dressings may further comprise an antibacterial agent in the first layer. The antibacterial agent may be one or more of iodine, penicillin, silver compounds, and erythromycin. The presence of an antibacterial agent is advantageous in promoting wound healing since many wounds do not heal quickly if there are too many bacteria present. Antibacterial agents also can allow for a longer time between changes of wound dressings.

Antiinflammatory

In some embodiments, any of the above-described two-layer wound dressings may further comprise an anti-inflammatory agent in the first layer. One of skill in the art would appreciate that excess inflammation may hinder wound healing.

Exemplary anti-inflammatory agents include steroids, such as hydrocortisone. It is particularly advantageous to include the anti-inflammatory compound in the wound dressing since undesirable effects can arise when administering steroids and other antinflammatory medications systemically. Use of an anti-inflammatory medication may allow for would healing may proceed more quickly with the minimization of scar tissue formation.

The following examples serve to describe more fully the manner of using the above described invention, as well as to set forth the best modes contemplated for carrying out various aspects of the invention. It is understood that these examples in no way serve to limit the true scope of this invention, but rather are presented for illustrative purposes.

EXAMPLE 1

Methods of Manufacturing and Processing Placental Collagen

The following preparations 1-5 are found in U.S. Pat. No. 5,002,071.

Preparation 1: Manufacture of Placental Collagen

In making the soft injectable material, fresh placentae were collected and the amnion is manually separated from the chorion, such as by finger separation. Both the amnion and the chorion are then cleaned of any remaining blood clots or debris. For short-term storage, the amnion and the chorion were placed in an antibiotic solution. Exemplary antibiotic solutions include linomycin (3 gms/10 ml), amphotericin B (50 mg/10 ml), neomycin sulfate (0.5 gm/10 ml), polymyxin B sulfate (500,000 units/10 ml) in 1 liter of normal saline until processed.

Collagen was extracted using limited proteolytic digestion with pepsin. In brief, tissue was homogenized in 0.5 M acetic acid, the pH was adjusted to 2.5 with HCl and the preparation was digested twice with pepsin (10 mg pepsin/gm wet weight tissue) overnight. A combination method of selective precipitation from neutral salt solvent and acid solvents was used to purify the collagen. Purified collagen was reconstituted by dialysis against low ionic strength sodium phosphate buffer (pH 7.2) at 15-17° C. Lidocaine was added to a final concentration of 0.3%. All procedures were carried out at 4-8° C., although other suitable temperatures can be used.

Preparation 2: Insoluble Amnion Processing

The following steps were taken to extract collagen from the amnion. The amnion is stored in an antibiotic solution according to Example 1. First, the antibiotic is decanted from the amnion. Then, 5 ml of cold distilled water is added to each amnion, with subsequent homogenization of the amnion for approximately 15 minutes in polytron. The homogenized amnion is then centrifuged at 8,000 Xg for 15 minutes at 4° C. The supernatant is then discarded and the precipitate washed five times with acetone to remove the lipids. The precipitate was then weighed, and pepsin (Sigma, 1:10,000, from porcine stomach mucosa) 3.0 molar acetic acid per amnion was added, 15 ml or more if extra large amnions, and the precipitate was homogenized for approximately 5 minutes in polytron.

The mixture was allowed to stand for 18 hours at 4.degree. C., centrifuged at 100,000.times.g for 1 hour at 4.degree. C., the supernatant was discarded, the precipitate weighed and then the pepsin and homogenization steps were repeated and the supernatant discarded.

Preparation 3: Soluble Amnion Processing

A presently preferred way of processing soluble amnions comprises rinsing the antibiotics from the amnions with deionized water, adding 5 ml of cold distilled water to each amnion, homogenizing for approximately 15 minutes in polytron and centrifuging at 8,000.times.g for 15 minutes at 4.degree. C. The supernatant was discarded and lipids were removed from the precipitate by washing with acetone three times and precipitate was weighed.

Pepsin (Sigma, 1:10,000, from porcine stomach mucosa) was added to the precipitate (1:100 w/w) and 100 ml of 0.5 molar acetic acid per amnion was added, more if the amnions are extra large, and then homogenized for approximately 10 minutes in polytron. The pepsin was allowed to extract collagen from the precipitate for 18 hours at 4.degree. C. and then centrifuged at 100,000.times.g for 1 hour at 4.degree. C. retaining both the precipitate and the supernatant. The supernatant is again weighed, and the steps of pepsin and acetic acid addition, homogenization, pepsin extraction of collagen and centrifuging are then repeated.

The supernatants from the first and second extractions are combined and 10-molar NaOH is added drop wise to adjust the pH to from 7.0 to 7.2. The mixture is permitted to stand for 2 hours at 4.degree. C., centrifuged at 100,000.times.g for 45 minutes at 4.degree. C. and the precipitate is discarded. NaCL to 3.0-molar is added to the supernatant and permitted to stand for 2 hours at 4.degree. C., centrifuged at 100,000.times.g for 45 minutes at 4.degree. C. and the precipitate is weighed and lidocaine to 0.3% is added.

Preparation 4: Soluble Amnion Processing with Further Purification

A presently preferred method of soluble amnion processing and further purification comprises rinsing the antibiotic from the amnion with deionized water, the amnions are cut to approximately 2 cm.times.2 cm and washed briefly with acetone, soaked in 0.5 M acetic acid (pH adjusted to 2.5 with HCl), homogenized with polytron for about 15 minutes, pepsin is added (1:100 pepsin/set tissue) (1 mg pepsin/1 ml solution) and stirred at 4° C. overnight, centrifuged as indicated above, the supernatant being retained. Pepsin was again added as indicated previously and stirred at 4° C. overnight, centrifuged and the supernatant from both centrifuging steps were combined and NaCL was added to 2 M and permitted to stand overnight at 4° C. and again centrifuged, the supernatant discarded and the precipitate retained.

The precipitate was purified by dissolving it in 0.5 M acetic acid, centrifuging, precipitate discarded, NaCL to 2 M was added to the supernatant, and it was permitted to stand overnight at 4.degree. C., again centrifuged with the supernatant discarded. The resulting precipitate was dissolved in 0.5 M acetic acid, again centrifuged, and the precipitate discarded. The supernatant was dialysed against 0.02 M Na.sub.2 HPO.sub.4 thoroughly for 48 hours with frequent dialysis fluid exchanges, centrifuged, the supernatant discarded, the precipitate weighed and solid lidocaine HCl was added to 0.30% with mechanical agitation.

Preparation 5: Chorion Processing

In a presently preferred method of processing soluble chorion the antibiotics were rinsed from the chorion with deionized water, the chorion was cut to approximately 2 cm.times.2 cm units and washed briefly with acetone and then soaked into 0.5 M acetic acid that had been adjusted to pH 2.5 with HCl. The tissue was then homogenized with polytron to fine particles for about 15 minutes, pepsin added and centrifuged as indicated above with the supernatant being retained. The pepsin and centrifuge steps were then repeated, the supernatant of each of these steps were combined and NaCl to 2 M was added and permitted to stand overnight at 4.degree. C. and then centrifuged again with the supernatant discarded.

For purification, the precipitate was dissolved into 0.5 M acetic acid, centrifuged and the precipitate discarded. NaCl to 2 M was added to the supernatant and permitted to stand overnight at 4.degree. C., then again centrifuged and the supernatant discarded. The precipitate was dissolved into 0.5 M acetic acid, centrifuged, dialysed against 0.02 M $Na_2HPO_4$ thoroughly for 48 hours with frequent dialysis fluid exchanges, again centrifuged, the supernatant discarded and the precipitate weighed. Solid lidocaine HCl was added to 0.30% to the precipitate with mechanical agitation.

EXAMPLE 2

Placental collagen is prepared, according to Preparation 1. The placental collagen is then subjected to radiation at 0.25 mRads until crosslinked. The crosslinked placental collagen is then prepared into a film that is applied to a healing wound.

Upon application to the healing wound, the film exhibits the following beneficial properties. The film reduces the rate of water evaporation from the wound. The film reduces the rate at which extraneous bacteria colonize or infect the wound. The film does not significantly reduce oxygen delivery to the wound. Upon changing the wound film, there is little loss of wound tissue to the wound. Furthermore, compared to other collagen wound films, the film prepared according to this example does not cause an allergic reaction or other immunogenic reaction.

EXAMPLE 3

A topical wound dressing is prepared as follows. Placental collagen is prepared that is derived from the insoluble amnion, according to Preparation 2. A mixture of type I and type III collagen is formed into a topical paste by adding zinc oxide to the collagen. Additionally, erythromycin and hydrocortisone are added to the topical wound dressing. The wound dressing is then applied to the wound and covered with a bandage. Improved wound healing is observed compared to a wound dressing comprising zinc oxide.

EXAMPLE 4

A topical wound dressing is prepared as follows. Placental collagen is prepared that is derived from the soluble amnion, according to Preparation 3. The placental collagen contains a ratio of 50% type III collagen and 50% type I collagen. There is no lodicane present in the formulation. The placental collagen formulation is 35 mg/mL collagen in saline solution that is isotonic relative to the wound tissue.

The mixture is then subjected to radiation at 0.25 mRads until crosslinked. Additionally, fibronectin is added to the mixture. The wound dressing is applied to a wound where excess unwanted scar tissue formation is of concern. The wound dressing is effective to inhibit excess scar tissue formation.

EXAMPLE 5

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. A second layer comprising gauze and a plastic adhesive material is applied to the first layer such that the second layer has a larger surface area than the first layer and can contact the skin surrounding the wound.

The wound dressing is then terminally sterilized, whereby the wound dressing is first frozen at a temperature below its freezing temperature, which is generally below 0° C., and irradiated with 7 kGray of radiation at an effective rate for a time effective to sterilize the collagen wound dressing. The wound dressing is then stored in a sterile environment before being applied to the wound.

EXAMPLE 6

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The collagen is then mixed with a hydrogel compound such that the hydrogel is evenly dispersed throughout the collagen.

A second layer comprising gauze and a plastic adhesive material is applied to the first layer such that the second layer has a larger surface area than the first layer and can contact the skin surrounding the wound. The plastic adhesive material is effective to reduce the rate of water evaporation from the wound.

The wound dressing is then terminally sterilized, whereby the wound dressing is first frozen at a temperature below its freezing temperature, which is generally below 0° C., and irradiated with 7 kGray of radiation at an effective rate for a time effective to sterilize the collagen wound dressing. The wound dressing is then stored in a sterile environment before being applied to the wound.

EXAMPLE 7

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises living skin cells harvested from the patient that are evenly dispersed throughout the collagen. A second layer comprising gauze and a plastic adhesive material is applied to the first layer such that the second layer has a larger surface area than the first layer and can contact the skin surrounding the wound.

EXAMPLE 8

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises fibrin and hyaluronic acid. A second layer comprising gauze and a plastic adhesive material is applied to the first layer such that the second layer has a larger surface area than the first layer and can contact the skin surrounding the wound.

When applied to a profusely bleeding wound, there is considerable blood clotting that is effective to reduce the rate of blood loss by 90% within ten minutes of application. There is little evidence of unwanted blood clotting occurring in portions of the vasculature away from the wound.

EXAMPLE 9

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises crosslinked-carboxymethylcellulose evenly dispersed throughout the collagen. A second layer comprising gauze and a plastic adhesive material is applied to the first layer such that the second layer has a larger surface area than the first layer and can contact the skin surrounding the wound.

When applied to a wound with considerable drainage, the wound dressing is effective to absorb nearly all of the drainage, requiring far fewer changes of the dressing over a given amount of time than a collagen wound dressing without the crosslinked-carboxy-methylcellulose.

EXAMPLE 10

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises stem cells isolated from the dermis of the patient's own skin. The first layer also comprises penicillin and erythromycin. A second layer comprising gauze and a plastic adhesive material is applied to the first layer such that the second layer has a larger surface area than the first layer and can contact the skin surrounding the wound. The wound dressing is effective to promote wound healing with minimal scar tissue as the stem cells are effective to populate the wound with sufficient epidermal cells to enhance the rate of granulation.

EXAMPLE 11

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises placental alkaline phosphatase. A second layer comprising gauze and a plastic adhesive material is applied to the first layer such that the second layer has a larger surface area than the first layer and can contact the skin surrounding the wound. The wound dressing is effective to enhance the rate of fibroblast production.

EXAMPLE 12

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises the growth factor EGF that is dispered evenly throughout the collagen layer. A second layer comprising gauze and a plastic adhesive material is applied to the first layer such that the second layer has a larger surface area than the first layer and can contact the skin surrounding the wound. The wound dressing is effective to enhance the rate of wound granulation as compared to collagen wound dressings without the EGF present in the first layer.

EXAMPLE 13

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises a mixture of penicillin and erythromycin that is dispered evenly throughout the collagen layer. A second layer comprising gauze and a plastic adhesive material is applied to the first layer such that the second layer has a larger surface area than the first layer and can contact the skin surrounding the wound. The wound dressing is effective to reduce the extent of bacterial colonization of the wound to an extent comparable with a two layer wound dressing that has been terminally sterilized.

EXAMPLE 14

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises a mixture of penicillin and erythromycin that is dispered evenly throughout the collagen layer. A second layer comprising gauze and a plastic adhesive material is applied to the first layer such that the second layer has a larger surface area than the first layer and can contact the skin surrounding the wound. The wound dressing is effective to reduce the extent of bacterial colonization of the wound to an extent comparable with a two layer wound dressing that has been terminally sterilized.

EXAMPLE 15

A two layer wound dressing is prepared as follows. The first layer is prepared of placental collagen. The placental collagen contains a ratio of 50% type III collagen and 50% type I collagen, at a total collagen concentration of 35 mg/mL, in saline solution that is isotonic relative to the wound tissue, and is crosslinked by exposure to 0.25 mRads of radiation. There is no lodicane present in the formulation. The first layer also comprises hydrocortisone, an anti-inflammatory compound. A second layer comprising gauze and a plastic adhesive material is applied to the first layer such that the second layer has a larger surface area than the first layer and can contact the skin surrounding the wound. The wound dressing is effective to reduce the degree of inflammation in the wound as compared to collagen wound dressings without hydrocortisone.

What is claimed is:

1. A wound dressing, consisting of:
a first layer comprising one or more types of sterilized collagen extracted from human placental tissue by proteolytic digestion of one or more of insoluble amnion from human placenta, soluble amnion from human placenta, and soluble chorion from human placenta, in a hydrogel effective to retain moisture when applied to a wound,
wherein the one or more types of sterilized collagen comprises at least 30% Type III collagen by weight of the total collagen in the first layer of the wound dressing,
wherein the first layer is exposed at least partially to contact wounded tissue: and
a second layer in contact with the first layer,
wherein the second layer comprises an adhesive compound effective to secure the wound dressing to a site in need of treatment.

2. The wound dressing of claim 1, wherein the hydrogel in the first layer is effective to retain moisture in the wound, and wherein the second layer further comprises a plastic compound effective to reduce a rate of water evaporation from the wound dressing.

3. The wound dressing of claim 1, wherein the first layer further comprises skin cells.

4. The wound dressing of claim 1, wherein the first layer further comprises a blood clotting agent selected from the group consisting of fibrin, vitamin K, and hyaluronic acid.

5. The wound dressing of claim 1, wherein the first layer further comprises a superabsorbent polymer effective to absorb blood from a bleeding wound and to stimulate blood clotting.

6. The wound dressing of claim 1, wherein the first layer further comprises placental alkaline phosphatase in an amount effective to stimulate proliferation of fibroblasts.

7. The wound dressing of claim 1, wherein the first layer further comprises stem cells selected from the group consisting of dermal stem cells, hair follicle bulge stem cells, placenta stem cells, and cord blood stem cells.

8. The wound dressing of claim 1, wherein the first layer further comprises a growth factor or a growth promoting serum factor selected from the group consisting of PDGF, EGF, TGF-alpha, TGF-beta, IGF-1, insulin, and combinations thereof.

9. The wound dressing of claim 1, wherein the first layer further comprises a polymer selected from the group consisting of hyaluronic acid, fibronectin, laminin, proteoglycans, and mixtures thereof.

10. The wound dressing of claim 1, wherein the first layer further comprises an antibacterial agent selected from the group consisting of iodine, penicillin, silver compounds, zinc oxide and erythromycin.

11. The wound dressing of claim 1, wherein the first layer further comprises an anti-inflammatory compound.

12. The wound dressing of claim 1, wherein the human placental tissue is selected from the group consisting of insoluble amnion, soluble amnion, and soluble chorion from human placenta.

13. The wound dressing of claim 1, wherein the second layer extends beyond the surface of the first layer.

14. The wound dressing of claim 1, wherein the collagen is crosslinked via gamma or electron beam irradiation.

15. The wound dressing of claim 1, wherein the collagen further comprises Type I collagen.

16. The wound dressing of claim 15, wherein the ratio of Type III collagen to Type I collagen in the mixture of Type I and Type III collagen is equal to or greater than about 50:50.

17. The wound dressing of claim 1, wherein the Type III collagen is 50% by weight of the total collagen present in the first layer of the wound dressing.

18. A method for dressing a wound in a subject, comprising the step of applying the wound dressing of claim 1 to a wound.

* * * * *